(12) United States Patent
Lauf et al.

(10) Patent No.: US 10,617,528 B2
(45) Date of Patent: Apr. 14, 2020

(54) ARTHROPLASTY IMPLANTS

(71) Applicant: Life Spine, Inc., Huntley, IL (US)

(72) Inventors: Garrett D. Lauf, Elgin, IL (US);
Daniel P. Predick, West Lafayette, IN (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 15/218,051

(22) Filed: Jul. 24, 2016

(65) Prior Publication Data

US 2017/0020678 A1 Jan. 26, 2017

Related U.S. Application Data

(60) Provisional application No. 62/196,588, filed on Jul. 24, 2015.

(51) Int. Cl.
| | |
|---|---|
| *A61F 2/30* | (2006.01) |
| *A61B 17/70* | (2006.01) |
| *A61B 17/56* | (2006.01) |
| *A61F 2/42* | (2006.01) |

(52) U.S. Cl.
CPC .......... *A61F 2/4225* (2013.01); *A61F 2/4241* (2013.01); *A61F 2002/305* (2013.01); *A61F 2002/3085* (2013.01); *A61F 2002/30331* (2013.01); *A61F 2002/30576* (2013.01);
(Continued)

(58) Field of Classification Search
CPC ............ A61B 17/7037; A61B 17/7032; A61B 17/8685; A61B 17/8605; A61B 17/864; A61B 17/7035; A61B 2017/681; A61B 17/7002; A61B 17/7082; A61B 17/70; A61B 17/8625; A61B 17/685; A61B 17/7001; A61F 2002/0888; A61F 2002/30433; A61F 2002/30507; A61F 2002/4629; A61F 2/0811; A61F 2/28; A61F 2/30749; A61F 2002/30405; A61F 2002/30411; A61F 2002/30438;
(Continued)

(56) References Cited

U.S. PATENT DOCUMENTS

| | | | | |
|---|---|---|---|---|
| 2007/0270839 | A1* | 11/2007 | Jeon | .................... A61B 17/7032 606/328 |
| 2008/0243191 | A1* | 10/2008 | Tipirneni | ............. A61B 17/742 606/280 |

(Continued)

*Primary Examiner* — Ann Schillinger
(74) *Attorney, Agent, or Firm* — Foley & Lardner LLP (57) ABSTRACT

Arthroplasty implants replace an articulating surface of a bone joint such as bone joints of the foot, and is characterized by a three-component device comprising a bone screw, a button, and a cap. The button incorporates knurling on its distal end to fixate onto bone, a center hole, a spherical pocket to mate with the bone screw for stabilization, and a proximal retention structure to mate with the cap. The bone screw incorporates distal bone (cortical) threads or threading, a spherical head, and a drive structure used to insert the bone screw through the hole of the button and into the bone (e.g. a distal segment of the first metatarsal). The cap incorporates a distal mating structure that retains the cap onto the button, a proximal smooth spherical head that mates with the distal surface of the bone (e.g. a phalange bone), and a tang that prevents rotation after implantation.

16 Claims, 8 Drawing Sheets

(52) U.S. Cl.
CPC ............. *A61F 2002/30836* (2013.01); *A61F 2002/4235* (2013.01); *A61F 2220/00* (2013.01)

(58) Field of Classification Search
CPC .. A61F 2002/30439; A61F 2002/30495; A61F 2002/305
See application file for complete search history.

(56) References Cited

U.S. PATENT DOCUMENTS

| | | | |
|---|---|---|---|
| 2009/0076550 A1* | 3/2009 | Bernhardt, Jr. .... | A61B 17/7032 606/246 |
| 2010/0241170 A1* | 9/2010 | Cammisa ........... | A61B 17/7032 606/264 |
| 2014/0228890 A1* | 8/2014 | Raju .................. | A61B 17/7035 606/270 |

* cited by examiner

Fig. 8

# ARTHROPLASTY IMPLANTS

CROSS-REFERENCE TO RELATED APPLICATIONS

This U.S. non-provisional patent application claims the benefit of and/or priority under 35 U.S.C. § 119(e) to U.S. provisional patent application Ser. No. 62/196,588 filed Jul. 24, 2015 titled "Arthroplasty Implants," the entire contents of which is specifically incorporated herein by reference.

FIELD OF THE INVENTION

The present invention relates to orthopedic implants and, particularly, to implants for replacing articulating surfaces of human bones.

BACKGROUND

Because of repeated use, disease, trauma or the like, the integrity and/or function of a joint of the human body may deteriorate. Osteoarthritis, for example, is a degenerative joint disease that causes a loss of cartilage in a joint. With joint deterioration there is joint pain, discomfort, and a loss of function. In order to attempt to relieve the pain and discomfort of joint problems, and in an effort to help restore function, non-surgical medical treatments are typically used first rather than surgical remedies. However, some situations require surgical remedies either as a first resort rather than a last resort.

Arthroplasty is one surgical remedy that can be used as a first option or when medical treatments no longer provide adequate relief from joint pain, discomfort, and/or disability (loss of function). Arthroplasty is an orthopedic surgical procedure where the articular surface of a musculoskeletal joint is replaced, remodeled, or realigned by osteotomy or some other process. This restores the integrity and function of a joint. In most of these cases a prosthesis or implant is also typically used.

There are many joints in the body where arthroplasty and/or joint replacements are routinely performed such as the hip, shoulder, and knee. To a lesser extent, arthroplasty and/or joint replacement is also performed in other joints in the body such as the hand and foot. However, arthroplasty and/or joint replacement for bones of the foot and the hand are becoming more common. In view of this, there are few or inferior arthroplasty implants for the bones of the foot and hand.

In view of the above, it is apparent that improvements can be made in arthroplasty implants. As such, it is desirable to have an arthroplasty implant that overcomes the deficiencies of the prior art. It is also desirable to have an arthroplasty implant that is not susceptible to shifts in position once installed. It is moreover desirable to have an arthroplasty implant for bones of the foot having the aforementioned attributes.

SUMMARY OF THE INVENTION

The present invention is an arthroplasty implant that replaces an articulating surface of a bone joint such as, but not limited to, bone joints of the foot such as a distal portion of the first metatarsal bone joint The arthroplasty implant is characterized by a three-component device comprising a bone screw, a button, and a cap.

The button incorporates knurling on its distal end to fixate onto bone, a center hole, a spherical pocket to mate with the bone screw for stabilization, and a proximal retention structure to mate with the cap. In one form, the proximal retention feature is an undercut. In another form, the proximal retention feature is a tang.

The bone screw incorporates distal bone (cortical) threads or threading, a spherical head, and a drive structure used to insert the bone screw through the hole of the button and into the bone (e.g. a distal segment of the first metatarsal).

The cap incorporates a distal mating structure that retains the cap onto the button, a proximal smooth spherical head that mates with the distal surface of the bone (e.g. a phalange bone), and a tang that prevents rotation after implantation. In one form, the distal mating structure is a distal undercut.

In use, the button is placed first on the proximal surface of a bone (e.g. the first metatarsal). The bone screw is then driven through the center hole of the button until the spherical head of the bone screw rests in the spherical pocket of the button, thereby stabilizing the construct. In one form, the cap is then placed onto the button until the retention structure of the button captures the mating structure of the cap, keeping the cap concentric with the button. In another form, the cap is then placed onto the button until the distal undercut mating (retention) structure of the cap mates with the proximal tang(s) retention structure of the button, keeping the cap concentric with the button. In both cases, the bone joint (e.g. metatarsophalangeal joint) is then placed back together with the distal surface of the phalange articulating against the smooth spherical head (end) of the cap.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate forms of the present invention, wherein.

DETAILED DESCRIPTION OF THE INVENTION

Referring to FIGS. 1-4, there is depicted an exemplary form of an arthroplasty implant, prosthesis, construct, or the like, generally designated 10, fashioned in accordance with the present principles, for replacing an articulating surface of a bone such as, but not limited to, a first metatarsal of the foot. The arthroplasty implant 10 is a three-part construct characterized by a bone screw 12, a cap 14, and a button 16, the three components fashioned from a known biocompatible implant material. It should be appreciated that the arthroplasty implants described herein may be used for extremity bones of the foot and hand. It may also be used for other bones.

The bone screw 12 is characterized by a body 18 defining a shaft 19 with external bone screw threads or threading 20. The threads 20 are preferably, but not necessarily, cortical bone screw threads, and extend generally from a distal end or tip of the shaft 19 to a proximate end of the shaft 19. The bone screw 12 is further characterized by a spherical head 21 having a curved (semi-spherical) underside 22 that tapers from a bevel 24 in the top 23 of the head 21 to the proximate end of the shaft 19. A drive structure 25 in the form of a configured socket is disposed in the top 23 of the head 21. The drive structure 25 is used to insert the bone screw 12 through a hole 49 of the button 16 (see, e.g., FIG. 2) and into a bone (e.g. a distal segment of the first metatarsal). As shown, the socket 25 is configured as a hexagonal socket that receives a hexagonal driving tool (not shown) such as is known in the art. Other configurations may be used.

The button 16 is characterized by a generally cup-shaped, annular body 40 having a generally annular ring portion 41 and a center hole 49 that extends from a top 44 of the body 40 to a beveled end opening 48 of the body 40. The body 40 incorporates knurling or the like on its distal end 42 (see, e.g. FIGS. 3, 4) to fixate onto bone, opening beveling 43, a spherical pocket 48 to mate with the bone screw head 22 for stabilization, and a proximal retention feature or structure 45, 46, 47 to mate with the cap 14 and particularly, with the distal mating structure (see below) of the cap 14. In one form, the proximal retention structure is generally an undercut 46 formed by an annular groove 47 creating a ledge 45 and undersurface 46 extending radially inwardly from the opening bevel 43. When implanted, the button 16 receives the bone screw 12 and the cap 14 to create an artificial joint articulation surface or structure.

Figure 1:
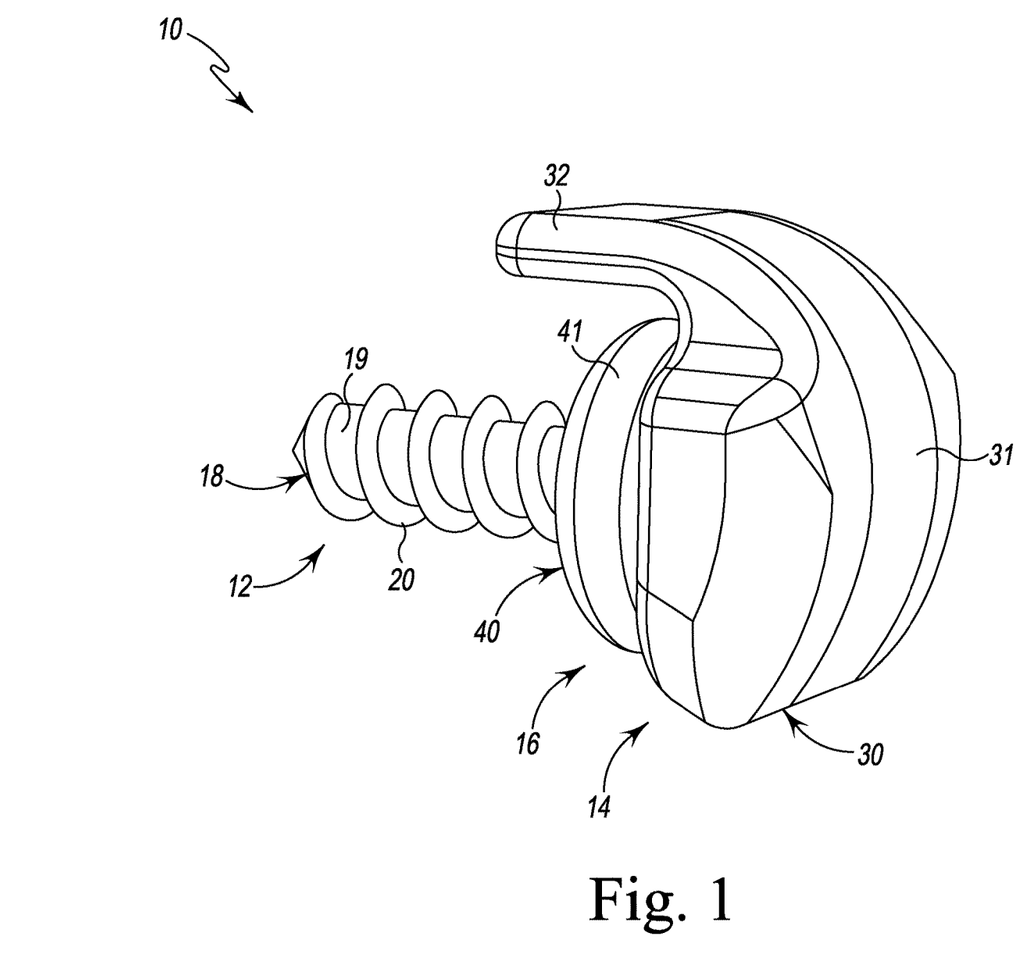
FIG. 1 is an isometric view of an exemplary embodiment of an arthroplasty implant fashioned in accordance with the present principles.
Figure 2:
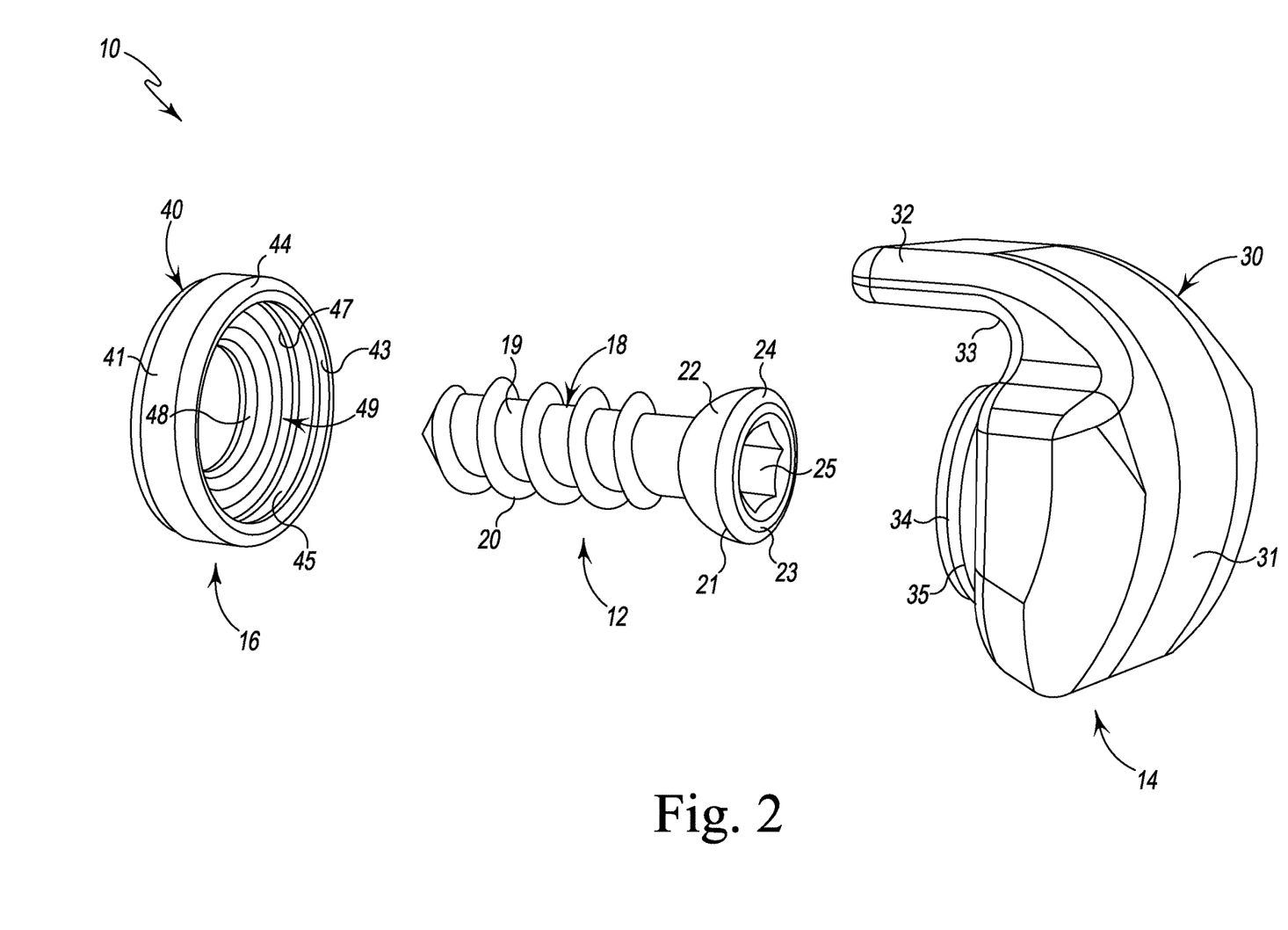
FIG. 2 is an exploded isometric view of the arthroplasty implant of FIG. 1.
Figure 3:
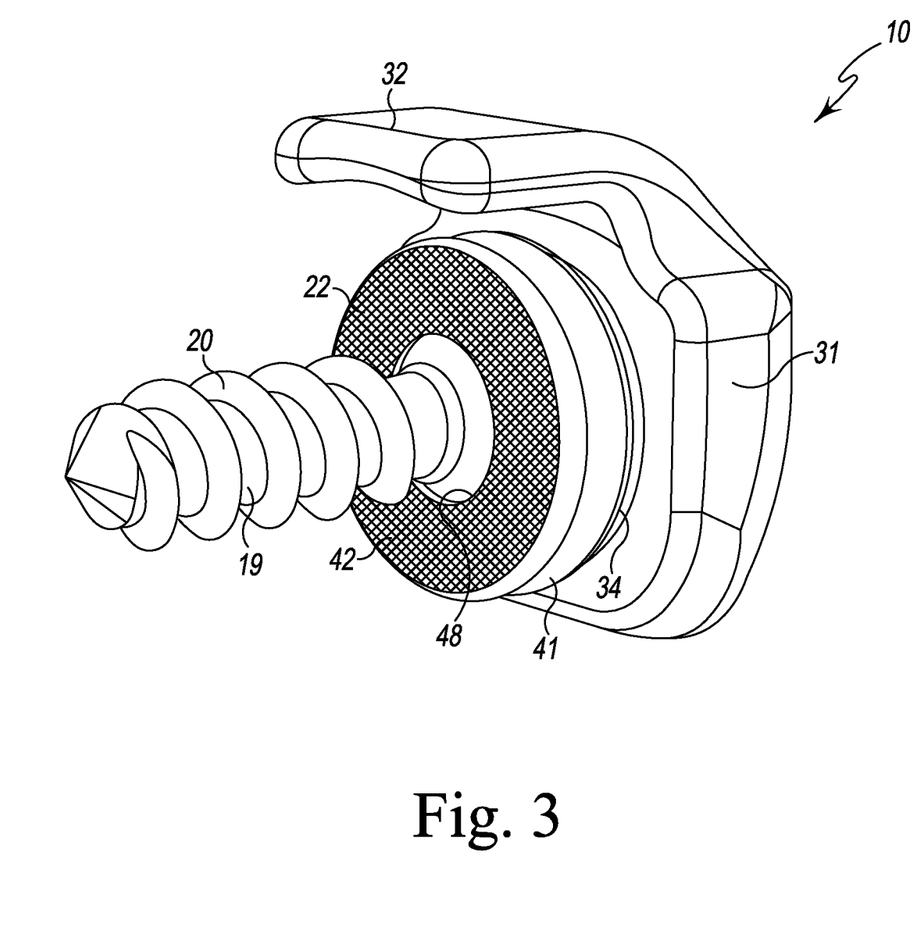
FIG. 3 is an isometric view of the arthroplasty implant of FIG. 1.
Figure 4:
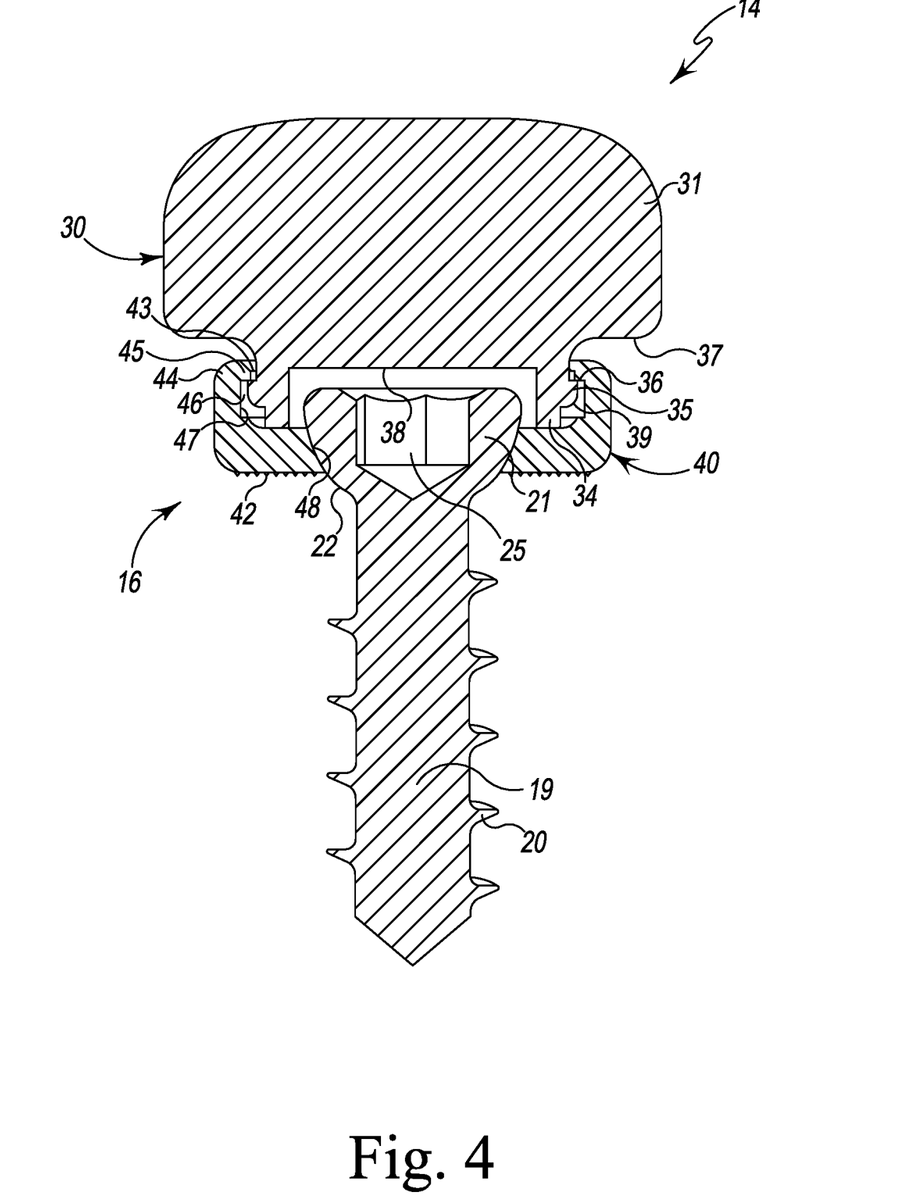
FIG. 4 is an enlarged sectional view of a portion of the arthroplasty implant of FIG. 1.
Figure 5:
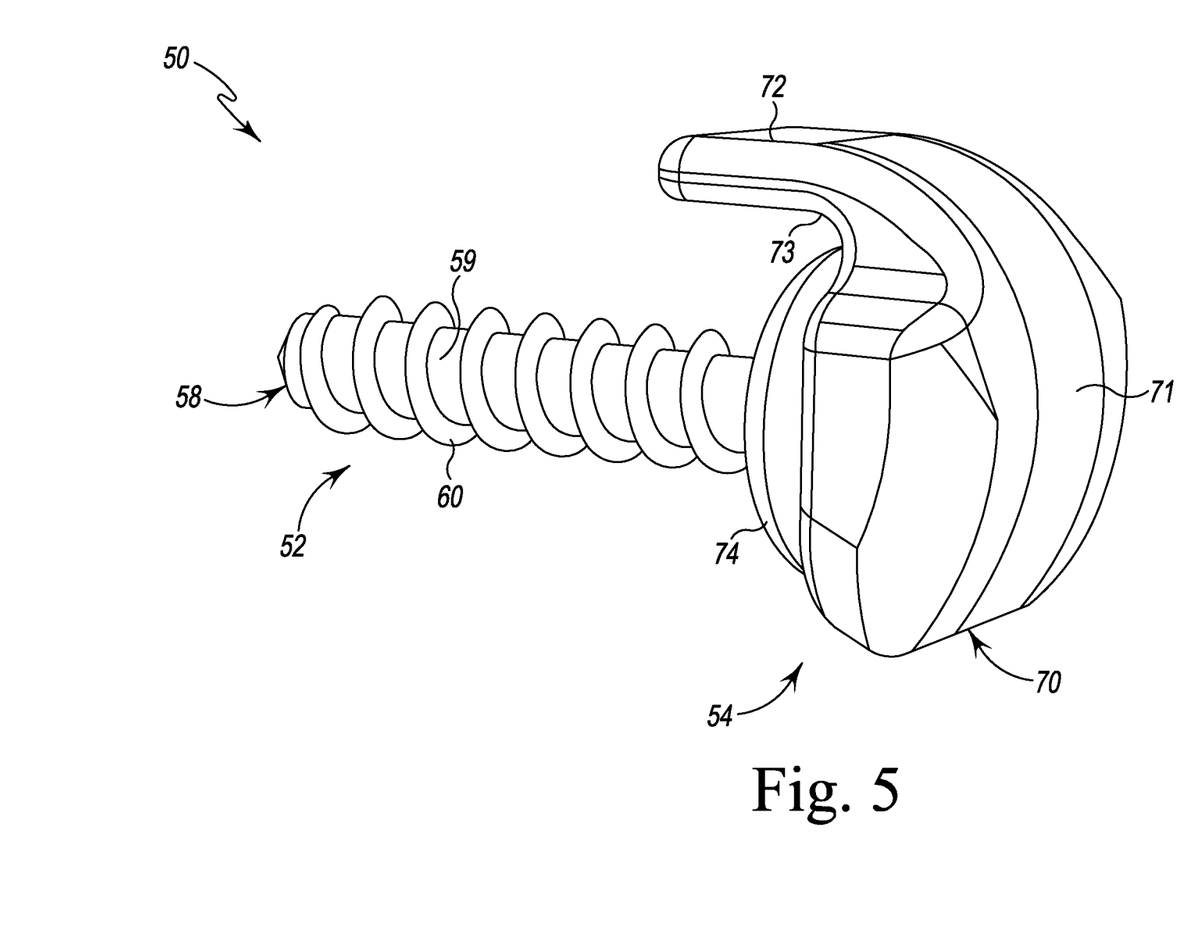
FIG. 5 is an isometric line drawing of another exemplary arthroplasty implant fashioned in accordance with the present principles.
Figure 6:
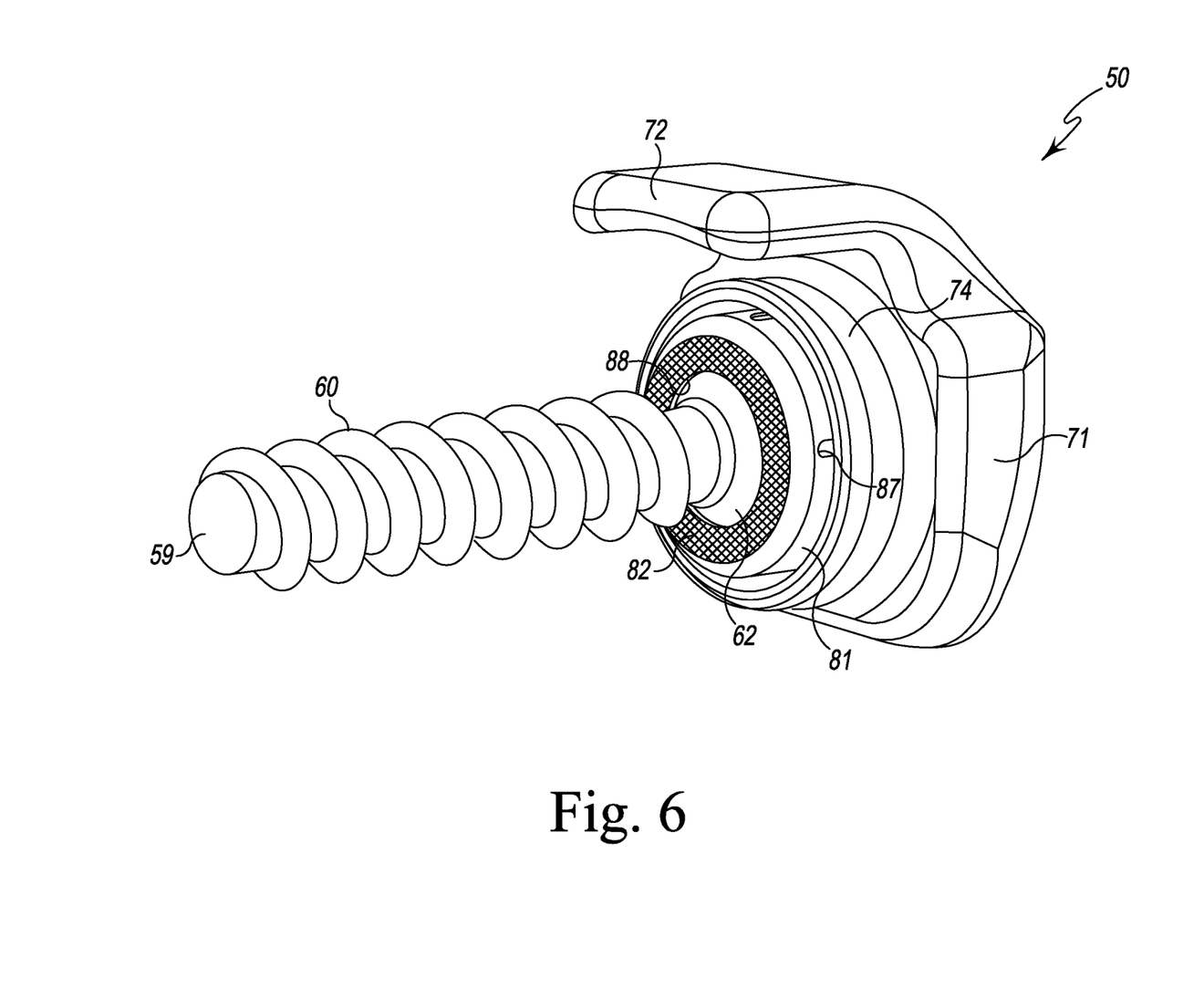
FIG. 6 is an isometric view of the arthroplasty implant of FIG. 5.

The cap 14 is characterized by a body 30 having a head 31 at its proximal end defining a smooth, curved outer articulation surface with an annular collar 34 on the distal or under side of the head 31, a tang 32 that prevents rotation after implantation, and a distal mating feature/structure 35, 36, 39. Preferably, but not necessarily, the outer curved articulation surface of the head 31 is curved in like manner to the articulation surface of the bone that the implant 10 will repair. The head 31 may have texturing, polishing, surfacing or the like as desired. As best seen in FIG. 4, the annular collar 34 defines a generally circular pocket 38 which receives the head 21 of the bone screw 12 once the implant 10 is installed or implanted. The distal mating structure of the cap 12 includes a rib or the like 35 that extends circumferentially about the outside surface of and radially outwardly from the collar 34 and defining an upper shelf or ledge 36. An annular bevel 39 is provided at the underside edge of the rib 35. The beveled, annular underside edge 39 cooperates with the annular beveled inlet 43 of the top 44 of the button 16.

The button 16 is placed first on the proximal surface of a bone (e.g. the proximal surface of the first metatarsal). The bone screw 12 is then driven through the center hole 49 of the button 16 until the spherical underside 22 of the head 21 of the bone screw 12 rests in the spherical pocket 48 of the button 16, thereby stabilizing the construct. The cap 14 is then placed onto the button 16 until the retention structure of the button captures the mating structure of the cap, keeping the cap 14 concentric with the button 16. Particularly, as the collar 34 of the cap 14 is pressed into the pocket 38 of the button 14, the underside annular edge bevel 39 of the rib 35 contacts the annular beveled inlet 43 of the top 44 of the button 16. Downward pressure causes the ledge 35 to snap into the annular groove 47 of the button 16. The undersurface 46 of the ledge 45 then extends over the shelf 36 of the rib 35 to retain the cap 14 onto the button 16.

Referring to FIGS. 5-8, there is depicted another an exemplary form of an arthroplasty implant, prosthesis, construct, or the like, generally designated 50, fashioned in accordance with the present principles, for replacing an articulating surface of a bone such as, but not limited to, a first metatarsal of the foot. The arthroplasty implant 50 is a three-part construct characterized by a bone screw 52, a cap 54, and a button 56, the three components fashioned from a known biocompatible implant material.

The bone screw 52 is characterized by a body 58 defining a shaft 59 with external bone screw threads or threading 60. The threads 60 are preferably, but not necessarily, cortical bone screw threads, and extend generally from a distal end or tip of the shaft 59 to a proximate end of the shaft 59. The bone screw 52 is further characterized by a spherical head 61 having a curved (semi-spherical) underside 62 that tapers from a bevel 64 in the top 63 of the head 61 to the proximate end of the shaft 59. A drive structure 65 in the form of a configured socket is disposed in the top 63 of the head 61. The drive structure 65 is used to insert the bone screw 52 through a hole 89 of the button 56 (see, e.g., FIG. 8) and into a bone (e.g. a distal segment of the first metatarsal). As shown, the socket 65 is configured as a hexagonal socket that receives a hexagonal driving tool (not shown) such as is known in the art. Other configurations may be used.

The button 56 is characterized by a generally cup-shaped, annular body 80 having a generally annular ring portion 81 and a center hole 89 that extends from a top 84 of the body 80 to a beveled end opening 88 of the body 80. The body 80 incorporates knurling or the like on its distal end 82 (see, e.g. FIGS. 6, 7) to fixate onto bone, opening beveling 83, a spherical pocket 88 to mate with the bone screw head 62 for stabilization, and a proximal retention feature or structure 85, 86, 87 to mate with the cap 54 and particularly, with the distal mating structure (see below) of the cap 54. In one form, the proximal retention structure is formed by an undercut or ledge 86 formed under an annular rim 85 that extends about the top 84 of the body 80, along with slits 87 in the top 84 of the body 80. An annular bevel 90 is provided at the top edge of the rim 85 that aids in connection between the button 56 and the cap 54. The slits 87 extend generally axial to the body 80 and allow the sections between the slits 87 to resiliently deform (expand and contract) to provide a "snap" fit between the cap 54 and the button 56.

Figure 7:
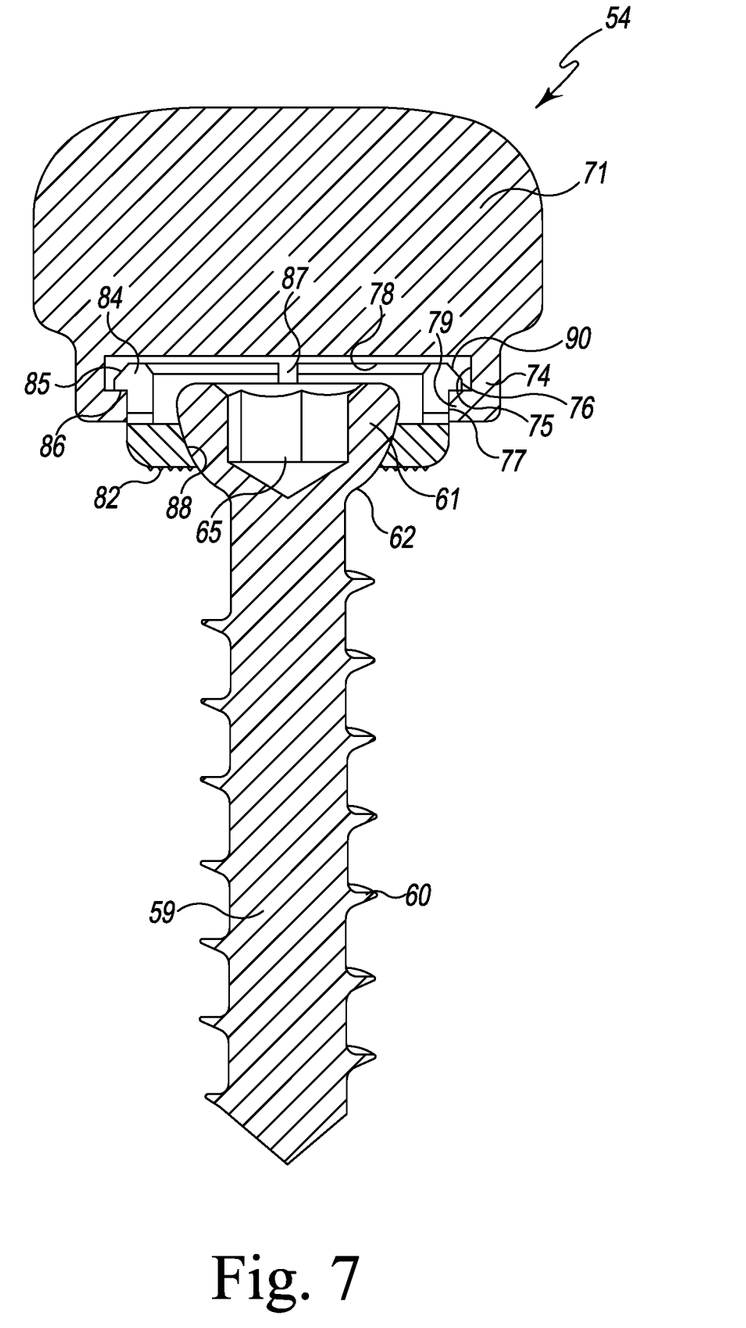
FIG. 7 is an enlarged sectional view of a portion of the arthroplasty implant of FIG. 5.
Figure 8:
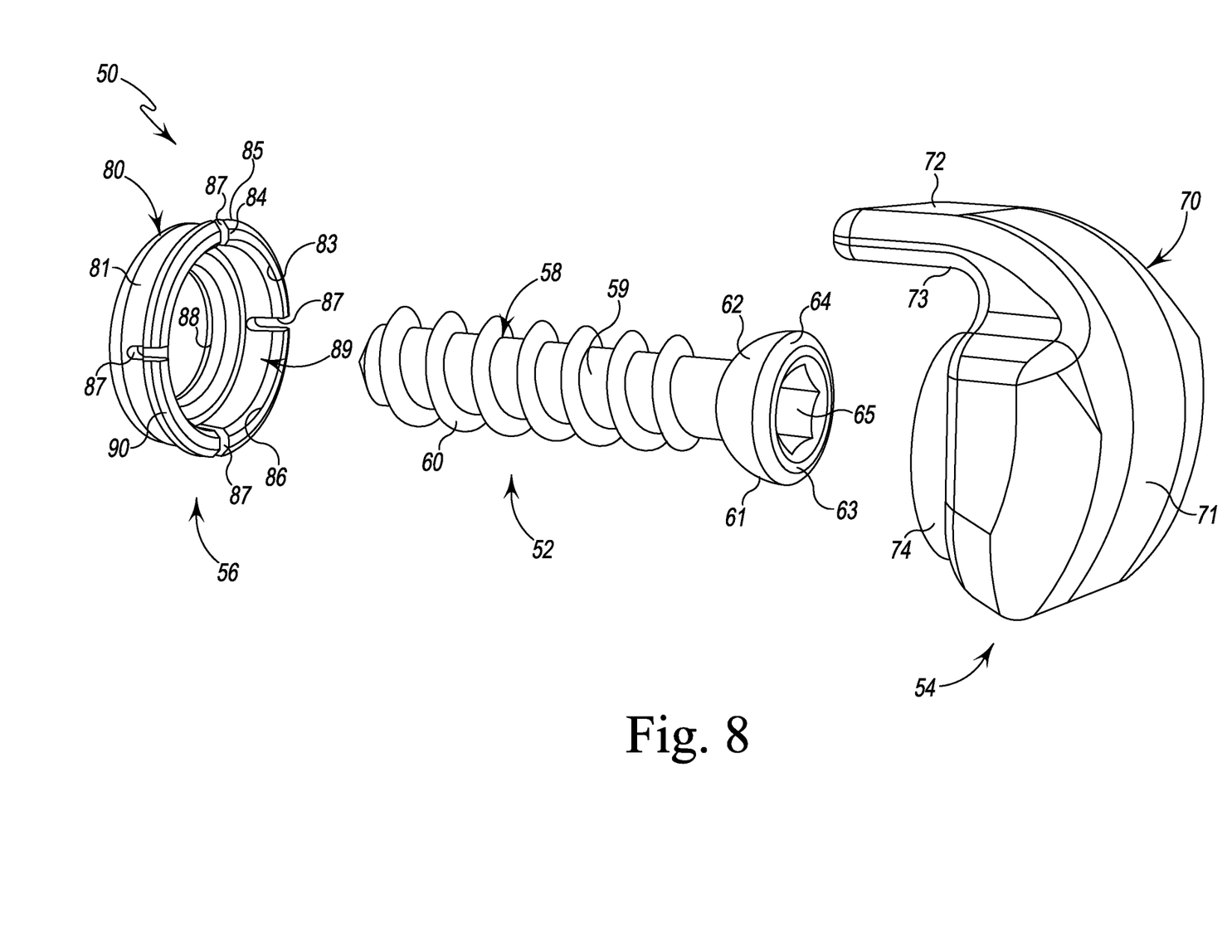
FIG. 8 is an exploded isometric view of the arthroplasty implant of FIG. 5.

The cap 54 is characterized by a body 70 having a head 71 at its proximal end defining a smooth, curved outer articulation surface with an annular stem or collar 74 on the distal or under side of the head 71, a tang 72 that prevents rotation after implantation, and a distal mating feature/structure 75, 76, 77, 79. Preferably, but not necessarily, the outer curved articulation surface of the head 71 is curved in like manner to the articulation surface of the bone that the implant 50 will repair. The head 71 may have texturing, polishing, surfacing or the like as desired. As best seen in FIG. 7, the annular stem 74 defines a generally circular pocket 78 which receives the head 61 of the bone screw 52 once the implant 50 is installed or implanted. The distal mating structure of the cap 52 includes a ridge or the like 79 that projects radially inward from the bottom of the stem 74. The ridge 79 defines an annular groove or channel 75 within the stem 74 and thus a shelf or ledge 76 on an upper surface of the ridge 79. An annular bevel 77 is provided at the underside inner edge of the ridge 79. The beveled, annular underside inner edge 79 cooperates with the annular bevel 90 at the top edge of the rim 85 of the button 56.

The button 56 is placed first on the proximal surface of a bone (e.g. the proximal surface of the first metatarsal). The bone screw 52 is then driven through the center hole 89 of the button 56 until the spherical underside 62 of the head 61 of the bone screw 52 rests in the spherical pocket 78 of the button 56, thereby stabilizing the construct. The cap 54 is then placed onto the button 56 until the retention structure of the button receives the mating structure of the cap, keeping the cap 54 concentric with the button 56. Particularly, as the collar 74 of the cap 54 is pressed over the button 56 and particularly the top 84 of the body 80, the underside annular inner bevel 77 of the ridge 79 contacts the annular bevel 90 at the top edge of the rim 85 of the button 56. Downward pressure causes the slit upper sides of the body 80 to resiliently compress the rim 85 to snap into the annular groove 75 of the button 56. Upon reception of the button into the cap, the slit upper sides of the body 80 return to their original shape. The undersurface 86 of the ledge 85 abuts the underside 86 of the ledge 85 to retain the cap 54 onto the button 56.

It should be appreciated that dimensions of the present arthroplasty implants' components, structures, and/or features can be altered as desired.

What is claimed is:

1. An implant for replacing an articulating surface of a bone joint, the implant comprising:
   a bone screw having a head with a top and a rounded underside, a shaft extending from the rounded underside of the head, bone threading on an outside surface of the shaft, and a drive structure in the top of the head configured to receive a drive tool for inserting the bone screw into bone of the bone joint;
   a button comprising:
      a proximal end and a distal end, the distal end configured to be received on bone of the bone joint and having an undersurface,
      a first pocket extending from the distal end and having a bore configured to allow the shaft of the bone screw to pass through but retain the underside of the head of the bone screw, and
      a retention structure comprising a ledge extending radially inwardly at the proximal end of the button to define an annular groove and an undercut on an undersurface of the ledge; and
   a cap comprising:
      a head having a distal surface and a curved proximal articulation surface, the curved proximal articulation surface configured to articulate with a bone joint, and
      an annular collar extending from the distal surface and having a mating structure, mating structure includes a rib extending radially outwardly from the annular collar;
   wherein rib of the mating structure engages the undercut of the retention structure by a snap engagement, whereby the cap is concentrically retained on the button;
   wherein the button defines a first outside lateral dimension and the head of the cap defines a second outside lateral dimension larger than the first outside lateral dimension.

2. The implant of claim 1, wherein:
   the undercut and the rib cooperate to prevent the cap from separating from the button once the cap has been received on the button.

3. The implant of claim 2, wherein:
   the undercut of the button is formed by a radially inwardly extending flange; and
   the rib of the cap is formed by a radially outwardly extending flange.

4. The implant of claim 3, wherein:
   the inwardly extending flange of the undercut comprises a first beveled surface;
   the outwardly extending flange of the rib slides across the beveled surface prior to engagement between the rib and the undercut.

5. The implant of claim 4, wherein the outwardly extending flange of the rib comprises a second beveled surface that slides across the first beveled surface of the inwardly extending flange during engagement between the rib and the undercut.

6. The implant of claim 1, wherein the bone threading of the bone screw comprises cortical bone threading.

7. The implant of claim 1, wherein the proximal surface of the cap is smooth.

8. The implant of claim 7, wherein the proximal surface of the cap is also rounded.

9. The implant of claim 1, wherein the first pocket of the button is spherical.

10. The implant of claim 1, wherein the annular collar defines a second pocket which receives the head of the bone screw.

11. An implant for replacing an articulating surface of a joint of a small bone of the foot or hand, the implant comprising:
    a bone screw having a head with a top and a spherical underside, a shaft extending from the spherical underside of the head, bone threading on an outside surface of the shaft, and a drive structure in the top of the head configured to receive a drive tool for inserting the bone screw into bone of the bone joint;
    an annular button comprising:
       a proximal end and a distal end, the distal end configured to be received on bone of the bone joint,
       a bone screw pocket extending from the distal end and having a bore configured to allow the shaft of the bone screw to pass through but retain the underside of the spherical head of the bone screw, and
       a retention structure comprising a ledge extending radially inwardly at the proximal end of the annular button to define an annular groove and an undercut on an undersurface of the ledge; and
    a cap comprising:
       a distal end and a proximal end, the proximal end having a curved proximal surface configured to articulate with an articulation surface of the bone joint, and
       an annular collar extending from the distal end of the cap, the annular collar having a pocket and a mating structure, wherein the pocket receives at least a portion of the head of the bone screw and the mating structure includes a rib extending radially outwardly from the annular collar;

wherein the rib on the mating structure engages the undercut of the retention structure by a snap-fit engagement, whereby the cap is retained on the annular button.

12. The implant of claim 11, wherein:
the ledge on the annular button comprises a first annular beveling on an upper edge of the ledge;
the rib on the cap comprises a second annular beveling on an underside edge of the rib.

13. The implant of claim 12, wherein:
the first annular beveling and the second annular beveling cooperate during engagement between the ledge and the rib;
the undercut on the annular button and the rib concentrically retains the cap on the annular button and to prevent the cap from separating from the annular button once the cap has been received on the annular button.

14. The implant of claim 11, wherein:
the cap comprises a tang; and
the tang is configured to prevent the cap from rotation of the annular button once the cap has been received on the button.

15. The implant of claim 11, wherein the bone threading of the bone screw comprises cortical bone threading.

16. The implant of claim 11, wherein the button defines a first lateral outside dimension and the head of the cap defines a second lateral outside dimension, wherein the second lateral outside dimension is larger than the first outside lateral dimension.

* * * * *